United States Patent [19]

Goetz et al.

[11] Patent Number: 4,538,009
[45] Date of Patent: Aug. 27, 1985

[54] PREPARATION OF SUBSTITUTED PHENOLS

[75] Inventors: Norbert Goetz, Limburgerhof; Harald Laas, Maxdorf; Peter Tavs, Limburgerhof; Leopold Hupfer, Friedelsheim; Karl Baer, Weinheim, all of Fed. Rep. of Germany

[73] Assignee: BASF Aktiengesellschaft, Ludwigshafen, Fed. Rep. of Germany

[21] Appl. No.: 599,574

[22] Filed: Apr. 12, 1984

[30] Foreign Application Priority Data

Apr. 20, 1983 [DE] Fed. Rep. of Germany ....... 3314372

[51] Int. Cl.³ .............................................. C07C 37/06
[52] U.S. Cl. .................................... 568/799; 568/740; 568/772
[58] Field of Search ........................ 568/799, 772, 740

[56] References Cited

U.S. PATENT DOCUMENTS 3,534,110 10/1970 Juguin et al. ........................ 568/799
3,801,651 4/1974 Adolphen et al. ................... 568/799
4,160,113 7/1979 Müller et al. ........................ 568/740
4,161,615 7/1979 Müller ................................. 568/740

FOREIGN PATENT DOCUMENTS 1426542 3/1976 United Kingdom ................ 568/740

Primary Examiner—Werren B. Lone
Attorney, Agent, or Firm—Oblon, Fisher, Spivak, McClelland & Maier

[57] ABSTRACT

Substituted phenols of the general formula I

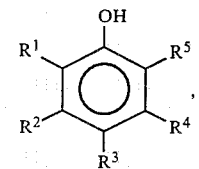

where $R^1$, $R^2$, $R^3$, $R^4$ and $R^5$ are each hydrogen or an aliphatic or aromatic hydrocarbon radical, are prepared by dehydrogenating a cyclic alcohol of the general formula II

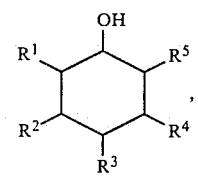

or a cyclic ketone of the general formula III

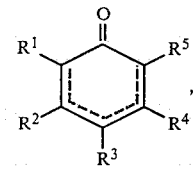

where one of the broken lines can be an additional C-C bond, in the gas phase at from 150° to 380° C. over a supported noble metal catalyst, by a process in which the dehydrogenation catalyst used is palladium or platinum on an aluminum spinel carrier, in particular an aluminum spinel which has a BET specific surface area of from 5 to 150 m²/g or, for the dehydrogenation of cyclohexenones, preferably from 10 to 50 m²/g. Particularly suitable aluminum spinels are those which, in addition to aluminum, contain magnesium, zinc, cobalt or nickel.

In the novel process, substituted phenols are obtained in high yields and selectivities, and the catalyst has an extremely long life without a significant decrease in activity.

14 Claims, No Drawings

PREPARATION OF SUBSTITUTED PHENOLS

The present invention relates to an improved process for the preparation of substituted phenols by dehydrogenating a 6-membered cyclic alcohol or a saturated or unsaturated ketone over a supported palladium or platinum catalyst.

The aromatization of 6-membered cyclic compounds to give phenols by means of elimination reactions, eg. dehydrogenation, dehydration or dehydrohalogenation, is a method which has long been known (Houben-Weyl, "Methoden der organischen Chemie" Volume 6/1 c, Part 2, pages 670 et seq.). Among these elimination reactions, dehydrogenation is without doubt the most important one industrially. The dehydrogenation of a large number of variously substituted cyclohexanols, cyclohexanones and cyclohexenones is described in the literature (loc. cit., pages 675–682), and one of the very important reactions is without doubt the conversion of 2,5,6- or 2,3,6-trimethylcyclohexenone to 2,3,6-trimethylphenol, which is a precursor of vitamin E.

A very advantageous process for the preparation of 2,3,6-trimethylphenol is described in British Pat. No. 1,258,963. In this process, the trimethylphenol is obtained by reacting diethyl ketone with methyl vinyl ketone or crotonaldehyde in the presence of a base, and dehydrogenating the resulting 2,3,6- or 2,3,5-trimethyl-2-cyclohexen-1-one in the gas phase.

In this patent, the catalysts for the gas-phase dehydrogenation are stated to be metals of group VIII of the periodic table, eg. iron, cobalt, nickel, rhodium, platinum or palladium, or metals or metal oxides of subgroup 1 of the periodic table, eg. copper or silver. The said patent also states that the metallic dehydrogenation catalysts are advantageously used on a conventional carrier, such as alumina, silica gel or active carbon. According to the examples, palladium catalysts with silica gel or active carbon as the carrier are used, and very good yields of 2,3,6-trimethylphenol are obtained. If the said dehydrogenation is carried out using the catalysts described in the stated patent and in a continuously operated apparatus, it is found that these catalysts give optimum results for only a short time, since their activity decreases appreciably after only a few hours.

It can be stated quite generally that the dehydrogenation of cyclic alcohols or ketones apparently takes place more readily the greater the extent to which the aromatic ring has already been formed. According to the literature, the majority of these reactions employ supported noble metal catalysts, in particular palladium on carbon. The reason for the strong preference for the neutral carbon carriers is probably due to the fact that acidic carriers, eg. silica gel, can promote dehydration as a side reaction, and alkaline carriers, eg. magnesium oxide or calcium oxide, can promote undesirable condensation reactions in the case of reactions involving ketones.

It is an object of the present invention to provide a dehydrogenation catalyst over which 6-membered cyclic alcohols and ketones can be advantageously dehydrogenated, even in a continuous process, ie. a distortion-resistant catalyst which permits the desired dehydrogenation to be carried out with high yield and selectivity and furthermore has a very long life without a significant decrease in activity.

We have found that this object is achieved, and that, surprisingly, the dehydrogenation of 6-membered cyclic alcohols or saturated or unsaturated ketones can be carried out with excellent conversions and yields, if a palladium or platinum catalyst on an aluminum spinel carrier is used. In particular, a catalyst of this type has good distortion-resistance and remains active for a long time.

The present invention accordingly relates to an improved process for the preparation of substituted phenols of the general formula I

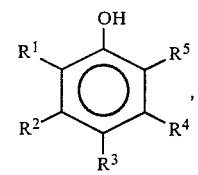

where $R^1$, $R^2$, $R^3$, $R^4$ and $R^5$ are each hydrogen or an aliphatic or aromatic hydrocarbon radical, by dehydrogenating a cyclic alcohol of the general formula II

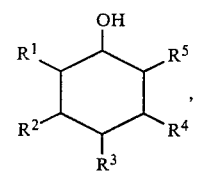

or a cyclic ketone of the general formula III

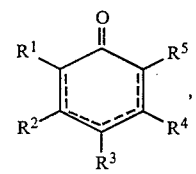

where one of the broken lines can be an additional C—C bond, in the gas phase at from 150° to 380° C. over a supported noble metal catalyst, wherein the dehydrogenation catalyst used is palladium or platinum on an aluminum spinel carrier.

The novel process takes place particularly advantageously if the catalyst used is a palladium or platinum catalyst on an aluminum spinel carrier which has a BET specific surface area of from 5 to 150 m²/g. The dehydrogenation of unsaturated cyclic ketones, ie. cyclohexenones, of the general formula III takes place particularly advantageously if the catalyst used is a palladium or platinum catalyst on the aluminum spinel carrier which has a BET specific surface area of from 10 to 50 m²/g. Particularly suitable carriers are aluminum spinels which, in addition to aluminum, contain magnesium, zinc, cobalt or nickel as a further spinel-forming metal.

Regarding methods for the determination of the BET specific surface area, reference may be made to the original literature: Brunauer, Emmett and Teller in J. Amer.Chem.Soc. 60 (1938), 309.

The novel process gives substituted phenols free from by-products which can result from dehydration or condensation reactions, complete conversion being achieved. A further advantage is the long life of the supported palladium of platinum/aluminum spinel catalysts used; for example, no decrease in activity was observed after continuous loading during an operating time of more than 1,500 hours. Palladium catalysts on aluminum spinel carriers are known, and have been used hitherto for other purposes, for example the selective gas-phase hydrogenation of phenol to give cyclohexanone (cf. German Laid-Open Application DOS 2,045,882) or the preparation of pyrocatechol or pyrocatechol monoethers from cyclohexanone derivatives (cf. German Laid-Open Applications DOS 2,064,097 and DOS 2,126,150). In the case of the lastmentioned reaction, however, satisfactory yields are obtained only when very special chromium-doped or titanium-doped palladium catalysts on lithium aluminum spinel carriers are used.

Suitable starting compounds of the general formulae II and III are essentially those in which $R^1$, $R^2$, $R^3$, $R^4$ and $R^5$ are each hydrogen, an aliphatic hydrocarbon radical of 1 to 10, preferably 1 to 4, carbon atoms, in particular methyl, or an aromatic hydrocarbon radical of 6 to 15 carbon atoms, preferably phenyl which is unsubstituted or substituted by one or more lower alkyl groups. Particularly important compounds of the formulae II and III are those in which 1, 2 or 3 of the radicals $R^1$, $R^2$, $R^3$, $R^4$ and $R^5$ are hydrocarbon radicals, while the others are each hydrogen.

Examples of suitable starting compounds are 2-, 3- and 4-methylcyclohexanol, 2,6-dimethylcyclohexanol, 3,5-dimethylcyclohexanol, 3,4-dimethylcyclohexanol, 2,3,6-trimethylcyclohexanol, 2,5,6-trimethylcyclohexanol, 2,6-diisopropylcyclohexanol, 2-methyl-6-ethylcyclohexanol, 2-methyl-6-butylcyclohexanol, 2,6-dimethyl-3-phenylcyclohexanol, 2-, 3- and 4-methylcyclohexanone, 2-methylcyclohex-2-en-1-one, 3-methylcyclohex-2-en-1-one, 4-methyl-cyclohex-2-en-1-one, 2,6-dimethylcyclohexanone, 2,6-dimethylcyclohex-2-en-1-one, 3,5-dimethylcyclohexanone, 3,4-dimethylcyclohexanone, 2,3,6-trimethylcyclohexanone, 2,3,6-trimethylcyclohex-2-en-1-one, 2,5,6-trimethylcyclohexanone, 2,5,6-trimethylcyclohex-2-en-1-one, 2,6-diisopropylcyclohexanone, 2-methyl-6-ethylcyclohexanone, 2-methyl-6-ethylcyclohex-2-en-1-one, 2-methyl-6-butylcyclohexanone and 2,6-dimethyl-3-phenylcyclohex-5-en-1-one.

A substantial advantage of the novel process is that mixtures of cyclic alcohols and cyclic ketones which are appropriately substituted can also be used without difficulty (see Example 3).

The catalyst system used in the process of the invention contains palladium or platinum on an aluminum spinel carrier, the noble metal content usually being from 0.05 to 15, preferably from 0.1 to 2, percent by weight, based on the carrier material.

Aluminum spinels are generally obtained by reacting aluminum oxide with a compound of a monovalent or divalent metal, eg. lithium, magnesium, cobalt, nickel, manganese or zinc (cf. Gmelin, system no. 35, Al, Tl, 1934–1935, and Ullmanns Encyklopädie der technischen Chemie, 3rd edition, 1955, vol. 6, pages 242–244). In principle, there are various possible methods for preparing the catalyst.

(a) The desired amount of the second spinel-forming component is applied onto Y-alumina extrudates or beads by impregnation with the corresponding aqueous nitrate or formate solutions, and the resulting product is dried at 150° C. To achieve spinel formation, the product obtained must then be heated for several hours (from 2 to 10 hours) at from 900° to 1300° C., preferably from 1000° to 1250° C.

(b) The two components, in the form of their oxides, eg. Y-alumina and magnesium oxide, are kneaded together in the required proportions, and the mixture is then heated at from 900° to 1300° C., preferably from 1000° to 1250° C.

(c) The two components are precipitated together as hydroxides from aqueous salt solutions, and, to achieve spinel formation, are then heated at from 900° to 1300° C., preferably from 1000° to 1250° C.

Depending on the temperatures and the heating times, preparation methods (a) to (c) give catalyst carriers which have specific surface areas of from 5 to 150 $m^2/g$. Especially for converting substituted cyclohexenones to substituted phenols by the process according to the invention, the carriers used should have a specific surface area of from 10 to 50 $m^2/g$, since only under this precondition are the long catalyst lives mentioned above achieved (for the preparation of this catalyst, see Example 1). For the conversion of substituted cyclohexanones and for the dehydrogenation of substituted cyclohexanols, this restriction in respect of the carrier used does not apply.

The noble metal is advantageously applied onto the ready-prepared carrier by impregnating the carrier material with an aqueous solution of the noble metal nitrate, and then, after the entire amount of solution has been absorbed, carrying out drying at from 100° to 140° C., preferably from 110° to 120° C. The catalysts are used in the form of beads or extrudates having a diameter of, for example, 3 mm and a length of 10 mm, or in the form of powders (for fluidized-bed furnaces) depending on the intended use. The catalyst is activated by heating it for several hours at the reaction temperature, in the presence of hydrogen.

To carry out the reaction according to the invention, the starting material of the formula II or III is passed over the activated catalyst at the dehydrogenation temperature. It is advantageous if an additional gas, eg. hydrogen or nitrogen, preferably hydrogen, is metered into the vapor of the starting material at the reactor inlet, in general a volume ratio of about 1:100 to 100:1 being chosen. The reaction temperatures used are from 150° to 380° C., preferably from 180° to 330° C. Solid starting materials of the formula II or III can be dissolved in a solvent before being fed to the reaction.

Suitable solvents are methanol, ethanol, n-butanol, tetrahydrofuran, dioxane, cyclohexyl methyl ether, n-methylmorpholine, anisole and toluene.

Another economic advantage of the novel process is that the saturated ketone which is always formed as a by-product in the industrial-scale dehydrogenation of unsaturated cyclic ketones, such as trimethylcyclohex-2-en-1-one, can be recycled to the process without difficulty. When conventional catalysts were used, recycling of the corresponding cyclohexanone was possible only to a limited extent. In contrast, the novel catalysts can be used to dehydrogenate trimethylcyclohexanone to trimethylphenol with high selectivity (cf. Example 1C).

The use of a palladium or platinum catalyst on an aluminum spinel has made it possible to carry out the gas-phase dehydrogenation of substituted 6-membered cyclic alcohols or ketones to give the corresponding phenols in an extremely economical continuous procedure. Using the novel process, substituted phenols are obtained in high yields and selectivities, and the catalyst has an extremely long life without a significant decrease in activity.

The substituted phenols prepared by the process of the invention are useful intermediates for a variety of uses; in particular, 2,3,6-trimethylphenol is a useful intermediate for vitamin E (cf. for example U.S. Pat. No. 3,692,839 and British Pat. No. 1,258,963).

EXAMPLE 1

A. Preparation of the catalyst 8,578 g of aluminum hydroxide containing 77.5% of $Al_2O_3$, and 1,776 g of technical-grade magnesium oxide containing 91.6% of MgO, were worked in a kneader, with the addition of water, until a shapable material was formed; this took about 3 hours. This material was converted to 4 mm extrudates, and these were dried for 16 hours at 120° C. and then heated for 3 hours at 520° C. The resulting material was then after-treated for 8 hours at 1150° C. After this treatment, the extrudates predominantly consisted of magnesium aluminum spinel which was of moderate to good crystalline quality and still contained a little well crystallised MgO and some $\alpha$-$Al_2O_3$. The extrudates had a BET specific surface area of from 17 to 19.5 m²/g.

1,714 g of the carrier thus obtained were then impregnated, in an impregnating drum, with 497 ml of a palladium nitrate solution containing 10.5 g of PdO. The product obtained was dried at 120° C. and then heated at 300° C. for 3 hours. The ready-prepared catalyst had a BET specific surface area of from 14 to 16 m²/g and contained 0.5% by weight of palladium.

B. Dehydrogenation of 2,3,6-trimethylcyclohex-2-en-1-one to 2,3,6-trimethylphenol 500 g of the catalyst prepared as described in Example 1A were activated for 24 hours in a stream of 20 liters (S.T.P.)/hour of hydrogen, in a reactor heated at 280° C. Thereafter, and likewise at 280° C., 180 g/hour of 96% pure 2,3,6-trimethylcyclohex-2-en-1-one, in vapor form, were passed concurrent with a stream of 20 liters (S.T.P.)/hour of hydrogen over the catalyst. The reaction product was then cooled and collected, the result after an operating time of 120 hours being as follows:

21.600 kg of 96% pure 2,3,6-trimethylcyclohex-2-en-1-one were converted, and 21.478 kg of reaction product were obtained; this product consisted of 85.4% by weight (corresponding to 18.342 kg) of 2,3,6-trimethylphenol and 11.6% by weight (corresponding to 2.491 kg) of 2,3,6-trimethylcyclohexan-1-one. Since the 2,3,6-trimethylcyclohexan-1-one can be readily separated off and recycled to the reaction zone or dehydrogenated separately to 2,3,6-trimethylphenol, the data found showed that 2,3,6-trimethylphenol was obtained with a selectivity of 97.5%.

C. Dehydrogenation of 2,3,6-trimethylcyclohexan-1-one to 2,3,6-trimethylphenol 180 g/hour of a mixture consisting of 62% of trimethylcyclohexanone, 19.5% of trimethylphenol and 18.5% of low boilers (predominantly cyclohexanols and straight-chain ketones) were passed, in vapor form, at 280° C. and concurrent with 20 liters (S.T.P.)/hour of hydrogen, over a catalyst prepared as described in Example 1A and activated as described in 1B. In the course of an operating time of 192 hours, 34.560 kg of mixture were converted. This corresponded to the following amounts of starting materials:

| | | |
|---|---|---|
| trimethylcyclohexanone | 21,427.2 g | = 150.9 moles |
| trimethylphenol | 6,739.2 g | = 49.6 moles |
| low boilers | 6,393.6 g | |

34.320 kg of reacted mixture having the following composition were obtained:

| | | |
|---|---|---|
| trimethylcyclohexanone | 4,839.1 g | = 34.1 moles |
| trimethylphenol | 22,136.4 g | = 162.8 moles |
| low boilers | 7,344.5 g | |

The conversion of trimethylcyclohexanone was accordingly 77.4% of theory, and the selectivity with respect to trimethylphenol was 96.9%.

EXAMPLE 2

Dehydrogenation of 2,6-dimethylcyclohexanol to 2,6-dimethylphenol

A catalyst in the form of extrudates and containing 0.5% by weight of palladium on a magnesium aluminum spinel carrier was introduced into a tube reactor having a capacity of 1 liter, and was brought to 270° C. (BET specific surface area: 122 m²/g). 100 g/hour of gaseous 2,6-dimethylcyclohexanol were passed, concurrent with 50 liters (S.T.P.)/hour of hydrogen, over this catalyst bed. As soon as it left the reactor, the reaction product was cooled, and worked up by distillation. In this procedure, 100 g of 2,6-dimethylcyclohexanol were converted to 91.5 g (yield: 96% of theory) of crystalline 2,6-dimethylphenol (mp. 49° C., bp. 203° C. under atmospheric pressure).

The reaction was carried out for 60 days as described above, without any decrease in catalyst activity being detected.

EXAMPLE 3

Using a procedure similar to that described in Example 2, 100 g/hour of a mixture consisting of 50% by weight of 2,6-dimethylcyclohexanol and 50% by weight of 2,6-dimethylcyclohexanone were converted, at 250° C. and under otherwise identical conditions, over the catalyst described in the stated example. This procedure gave 2,6-dimethylphenol in a yield of 97% of theory.

EXAMPLE 4

The procedure described in Example 2 was followed, except that the catalyst used contained 0.5% by weight of palladium on a zinc aluminum spinel carrier (BET specific surface area 144 m²/g). 2,6-dimethyl-3-phenyl-cyclohexanone was converted to 2,6-dimethyl-3-phenylphenol (bp.=118° C./0.2 mbar) in a yield of 94% of theory.

EXAMPLE 5

The procedure described in Example 2 was followed, except that the catalyst used contained 0.5% by weight of palladium on a cobalt aluminum spinel carrier (BET specific surface area 138 m²/g). 2,6-dimethyl-3-(p-methylphenyl)-cyclohexanone was converted to 2,6-dimethyl-3-(p-methylphenyl)-phenol (bp.=129° C./0.2 mbar) in a yield of 91% of theory.

EXAMPLE 6

The procedure described in Example 2 was followed, except that the catalyst used contained 0.5% by weight of palladium on a nickel aluminum spinel carrier (BET specific surface area 117 m²/g). 3-methyl-2-cyclohexen-1-oone was converted to m-cresol (bp.=202° C.) in a yield of 97% of theory.

EXAMPLE 7

500 ml of catalyst were introduced into a fluidized-bed reactor having a capacity of 0.7 liter. The catalyst contained 0.25% by weight of platinum on a magnesium aluminum spinel carrier and had a particle size of from 0.2 to 0.6 mm and a BET specific surface area of 125 m²/g. The temperature of the reactor was brought to 275° C., and the mixture which was preheated to this temperature and consisted of 200 liters/hour of nitrogen and 20 liters/hour of hydrogen was passed in. 60 g/hour of gaseous 2,6-dimethylcyclohexanol were passed continuously through the fluidized catalyst bed produced in this manner. The reaction product was obtained by cooling the exit gases, and was distilled. 100 g of 2,6-dimethylcyclohexanol were converted to 90.5 g (yield: 95% of theory) of 2,6-dimethylphenol.

EXAMPLE 8

The procedure described in Example 7 was followed, except that the reaction temperature was 230° C. and the catalyst used contained 1.5% by weight of palladium on a zinc aluminum spinel carrier. 2-sec.-butylcyclohexanol was converted to 2-sec.-butylphenol (bp.=227°-228° C.) in a yield of 94% of theory.

EXAMPLE 9

The procedure described in Example 7 was followed, except that the catalyst used contained 0.5% by weight of platinum on a magnesium aluminum spinel carrier. 2,6-diisopropylcyclohexanol was converted to 2,6-diisopropylphenol (bp.=255°-256° C.) in a yield of 96.5% of theory.

We claim:

1. An improved process for the preparation of a substituted phenol of the formula I

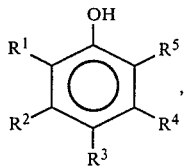

where R¹, R², R³, R⁴ and R⁵ are each independently hydrogen or an aliphatic or aromatic hydrocarbon radical, by dehydrogenating a cyclic alcohol of the formula II

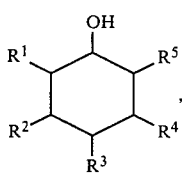

or a cyclic ketone of the formula III

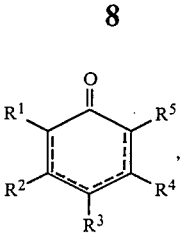

where one of the broken lines can be an additional C—C bond, in the gas phase at from 150° to 380° C. over a supported noble metal catalyst, wherein the dehydrogenation catalyst used is palladium or platinum on an aluminum spinel carrier which, in addition to aluminum, contains magnesium, zinc, cobalt or nickel.

2. A process for the preparation of a substituted phenol of the formula I as claimed in claim 1, wherein the catalyst used is palladium or platinum on an aluminum spinel carrier which has a BET specific surface area of from 5 to 150.

3. A process for the preparation of a substituted phenol of the formula I as claimed in claim 1, wherein the dehydrogenation of an unsaturated cyclic ketone of the formula III is carried out using a palladium or platinum catalyst on an aluminum spinel carrier which has a BET specific surface area of from 10 to 50 m²/g.

4. The process of claim 1, wherein R¹, R², R³, R⁴ and R⁵ are each independently a hydrogen or an aliphatic hydrocarbon radical of C₁₋₁₀.

5. The process of claim 1, wherein R¹, R², R³, R⁴ and R⁵ are each independently a hydrogen or an aliphatic hydrocarbon radical of C₁₋₄.

6. The process of claim 1, wherein R¹, R², R³, R⁴ and R⁵ are each independently hydrogen or an aromatic hydrocarbon radical of C₆₋₁₅.

7. The process of claim 1, wherein at least one of the radicals R¹, R², R³, R⁴ and R⁵ is a hydrocarbon radical, the other each being hydrogen.

8. The process of claim 1, wherein at least two of the radicals R¹, R², R³, R⁴ and R⁵ are hydrocarbon radicals, the others each being hydrogen.

9. The process of claim 1, wherein at least three of the radicals R¹, R², R³, R⁴ and R⁵ are hydrocarbon radicals, the others each being hydrogen.

10. The process of claim 1, wherein the cyclic alcohol is at least one member selected from the group consisting of 2-methylcyclohexanol, 3-methylcyclohexanol, 4-methylcyclohexanol, 2,6-dimethylcyclohexanol, 3,5-dimethylcyclohexanole, 3,4-dimethylcyclohexanol, 2,3,6-trimethylcyclohexanol, 2,5,6-trimethylcyclohexanol, 2,6-diisopropylcyclohexanol, 2-methyl-6-ethylcyclohexanol, 2-methyl-6-butylcyclohexanol, 2,6-dimethyl-3-phenylcyclohexanol or a mixture thereof.

11. The process of claim 1, wherein the cyclo ketone is at least one member selected from the group consisting of 2-methylcyclohexanone, 3-methylcyclohexanone, 4-methylcyclohexanone, 2-methylcyclohex-2-en-1-one, 3-methylcyclohex-2-en-1-one, 4-methylcyclohex-2-en-1-one, 2,6-dimethylcyclohexanone, 2,6-dimethylcyclohex-2-en-1-one, 3,5-dimethylcyclohexanone, 3,4-dimethylcyclohexanone, 2,3,6-trimethylcyclohexanone, 2,3,6-trimethylcyclohex-2-en-1-one, 2,5,6-tri-methylcyclohexanone, 2,5,6-trimethylcyclohex-2-en-1-one, 2,6-diisopropylcyclohexanone, 2-methyl-6-ethylcyclohexanone, 2-methyl-6-ethylcyclohex-2-en-1-one, 2-methyl-6-butylcyclohexanone, 2,6-dimethyl-3-phenylcyclohex-5-en-1-one or a mixture thereof.

12. The process of claim 1, wherein a mixture of a cyclic alcohol of the formula II and a cyclic ketone of formula III is used.

13. The process of claim 1, wherein palladium or platinum are each present in an amount of from 0.05 to 15% by weight.

14. The process of claim 1, wherein palladium or platinum are each present in an amount of from 0.1 to 2% by weight.

* * * * *